(12) United States Patent
Olivera et al.

(10) Patent No.: US 7,639,853 B2
(45) Date of Patent: Dec. 29, 2009

(54) METHOD OF AND SYSTEM FOR PREDICTING DOSE DELIVERY

(75) Inventors: Gustavo H. Olivera, Madison, WI (US); Kenneth J. Ruchala, Madison, WI (US); Eric Schnarr, McFarland, WI (US); Jeffrey M. Kapatoes, Madison, WI (US); Weiguo Lu, Madison, WI (US); Jason Haimerl, Lake Mills, WI (US); John H. Hughes, Madison, WI (US); Thomas R. Mackie, Verona, WI (US)

(73) Assignee: TomoTherapy Incorporated, Madison, WI (US)

( * ) Notice: Subject to any disclaimer, the term of this patent is extended or adjusted under 35 U.S.C. 154(b) by 141 days.

(21) Appl. No.: 11/459,066

(22) Filed: Jul. 21, 2006

(65) Prior Publication Data
US 2007/0041495 A1 Feb. 22, 2007

Related U.S. Application Data

(60) Provisional application No. 60/701,580, filed on Jul. 22, 2005.

(51) Int. Cl.
*G06K 9/00* (2006.01)
*A61B 5/05* (2006.01)
(52) U.S. Cl. .................. 382/128; 382/131; 600/427
(58) Field of Classification Search .......... 382/128, 382/131; 600/427
See application file for complete search history.

(56) References Cited

U.S. PATENT DOCUMENTS

| | | |
|---|---|---|
| 3,949,265 A | 4/1976 | Holl |
| 3,964,467 A | 6/1976 | Rose |
| 4,006,422 A | 2/1977 | Schriber |
| 4,032,810 A | 6/1977 | Eastham et al. |
| 4,149,081 A | 4/1979 | Seppi |
| 4,181,894 A | 1/1980 | Pottier |
| 4,189,470 A | 2/1980 | Rose |
| 4,208,185 A | 6/1980 | Sawai et al. |
| 4,273,867 A | 6/1981 | Lin et al. |

(Continued)

FOREIGN PATENT DOCUMENTS

CA 2091275 9/1993

(Continued)

OTHER PUBLICATIONS

Rueckert et al., Nonrigid registration using free-form deformations: applications to breast mr images, 1999, IEEE, pp. 712-721.*

(Continued)

*Primary Examiner*—John B Strege
(74) *Attorney, Agent, or Firm*—Michael Best & Friedrich LLP (57) ABSTRACT

A system and method of predicting a radiation dose to be delivered to a patient. The method includes the acts of generating a first image of at least a portion of the patient, defining a treatment plan for the patient, generating a second image of at least a portion of the patient while the patient is substantially in a treatment position, updating the patient profile with the second image, and predicting the radiation dose to be delivered to the patient based upon the patient profile and the treatment plan.

25 Claims, 8 Drawing Sheets

U.S. PATENT DOCUMENTS

| | | | |
|---|---|---|---|
| 4,314,180 A | 2/1982 | Salisbury | |
| 4,335,465 A | 6/1982 | Christiansen et al. | |
| 4,388,560 A | 6/1983 | Robinson et al. | |
| 4,393,334 A | 7/1983 | Glaser | |
| 4,395,631 A | 7/1983 | Salisbury | |
| 4,401,765 A | 8/1983 | Craig et al. | |
| 4,426,582 A | 1/1984 | Orloff et al. | |
| 4,446,403 A | 5/1984 | Cuomo et al. | |
| 4,480,042 A | 10/1984 | Craig et al. | |
| 4,570,103 A | 2/1986 | Schoen | |
| 4,664,869 A | 5/1987 | Mirzadeh et al. | |
| 4,703,018 A | 10/1987 | Craig et al. | |
| 4,715,056 A | 12/1987 | Vlasbloem et al. | |
| 4,736,106 A | 4/1988 | Kashy et al. | |
| 4,752,692 A | 6/1988 | Jergenson et al. | |
| 4,754,760 A | 7/1988 | Fukukita et al. | |
| 4,815,446 A | 3/1989 | McIntosh | |
| 4,818,914 A | 4/1989 | Brodie | |
| 4,868,844 A | 9/1989 | Nunan | |
| 4,870,287 A | 9/1989 | Cole et al. | |
| 4,879,518 A | 11/1989 | Broadhurst | |
| 4,912,731 A | 3/1990 | Nardi | |
| 4,936,308 A | 6/1990 | Fukukita et al. | |
| 4,987,309 A | 1/1991 | Klasen et al. | |
| 4,998,268 A | 3/1991 | Winter | |
| 5,003,998 A | 4/1991 | Collett | |
| 5,008,907 A | 4/1991 | Norman et al. | |
| 5,012,111 A | 4/1991 | Ueda | |
| 5,065,315 A | 11/1991 | Garcia | |
| 5,073,913 A | 12/1991 | Martin | |
| 5,084,682 A | 1/1992 | Swenson et al. | |
| 5,107,222 A | 4/1992 | Tsuzuki | |
| 5,124,658 A | 6/1992 | Adler | |
| 5,210,414 A | 5/1993 | Wallace et al. | |
| 5,250,388 A | 10/1993 | Schoch, Jr. et al. | |
| 5,317,616 A | 5/1994 | Swerdloff et al. | |
| 5,335,255 A | 8/1994 | Seppi et al. | |
| 5,346,548 A | 9/1994 | Mehta | |
| 5,351,280 A | 9/1994 | Swerdloff et al. | |
| 5,382,914 A | 1/1995 | Hamm et al. | |
| 5,391,139 A | 2/1995 | Edmundson | |
| 5,394,452 A | 2/1995 | Swerdloff et al. | |
| 5,405,309 A | 4/1995 | Carden, Jr. | |
| 5,442,675 A | 8/1995 | Swerdloff et al. | |
| 5,453,310 A | 9/1995 | Andersen et al. | |
| 5,466,587 A | 11/1995 | Fitzpatrick-McElligott et al. | |
| 5,471,516 A | 11/1995 | Nunan | |
| 5,483,122 A | 1/1996 | Derbenev et al. | |
| 5,489,780 A | 2/1996 | Diamondis | |
| 5,523,578 A | 6/1996 | Herskovic | |
| 5,528,650 A | 6/1996 | Swerdloff et al. | |
| 5,548,627 A | 8/1996 | Swerdloff et al. | |
| 5,576,602 A | 11/1996 | Hiramoto et al. | |
| 5,578,909 A | 11/1996 | Billen | |
| 5,581,156 A | 12/1996 | Roberts et al. | |
| 5,596,619 A | 1/1997 | Carol | |
| 5,596,653 A | 1/1997 | Kurokawa | |
| 5,621,779 A | 4/1997 | Hughes et al. | |
| 5,622,187 A | 4/1997 | Carol | |
| 5,625,663 A | 4/1997 | Swerdloff et al. | |
| 5,627,041 A | 5/1997 | Shartle | |
| 5,641,584 A | 6/1997 | Andersen et al. | |
| 5,647,663 A | 7/1997 | Holmes | |
| 5,651,043 A | 7/1997 | Tsuyuki et al. | |
| 5,661,377 A | 8/1997 | Mishin et al. | |
| 5,661,773 A | 8/1997 | Swerdloff et al. | |
| 5,667,803 A | 9/1997 | Paronen et al. | |
| 5,668,371 A | 9/1997 | Deasy et al. | |
| 5,673,300 A | 9/1997 | Reckwerdt et al. | |
| 5,692,507 A | 12/1997 | Seppi et al. | |
| 5,695,443 A | 12/1997 | Brent et al. | |
| 5,712,482 A | 1/1998 | Gaiser et al. | |
| 5,721,123 A | 2/1998 | Hayes et al. | |
| 5,724,400 A | 3/1998 | Swerdloff et al. | |
| 5,729,028 A | 3/1998 | Rose | |
| 5,734,168 A | 3/1998 | Yao | |
| 5,747,254 A | 5/1998 | Pontius | |
| 5,751,781 A | 5/1998 | Brown et al. | |
| 5,753,308 A | 5/1998 | Andersen et al. | |
| 5,754,622 A | 5/1998 | Hughes | |
| 5,754,623 A | 5/1998 | Seki | |
| 5,760,395 A | 6/1998 | Johnstone | |
| 5,802,136 A | 9/1998 | Carol | |
| 5,811,944 A | 9/1998 | Sampayan et al. | |
| 5,815,547 A | 9/1998 | Shepherd et al. | |
| 5,818,058 A | 10/1998 | Nakanishi et al. | |
| 5,818,902 A | 10/1998 | Yu | |
| 5,820,553 A | 10/1998 | Hughes | |
| 5,821,051 A | 10/1998 | Androphy et al. | |
| 5,821,705 A | 10/1998 | Caporaso et al. | |
| 5,834,454 A | 11/1998 | Kitano et al. | |
| 5,836,905 A | 11/1998 | Lemelson et al. | |
| 5,842,175 A | 11/1998 | Andros et al. | |
| 5,866,912 A | 2/1999 | Slater et al. | |
| 5,870,447 A | 2/1999 | Powell et al. | |
| 5,877,023 A | 3/1999 | Sautter et al. | |
| 5,877,192 A | 3/1999 | Lindberg et al. | |
| 5,912,134 A | 6/1999 | Shartle | |
| 5,920,601 A | 7/1999 | Nigg et al. | |
| 5,953,461 A | 9/1999 | Yamada | |
| 5,962,995 A | 10/1999 | Avnery | |
| 5,963,615 A | 10/1999 | Egley et al. | |
| 5,969,367 A | 10/1999 | Hiramoto et al. | |
| 5,977,100 A | 11/1999 | Kitano et al. | |
| 5,983,424 A | 11/1999 | Naslund | |
| 5,986,274 A | 11/1999 | Akiyama et al. | |
| 6,011,825 A | 1/2000 | Welch et al. | |
| 6,020,135 A | 2/2000 | Levine et al. | |
| 6,020,538 A | 2/2000 | Han et al. | |
| 6,029,079 A | 2/2000 | Cox et al. | |
| 6,038,283 A | 3/2000 | Carol et al. | |
| 6,049,587 A | 4/2000 | Leksell et al. | |
| 6,066,927 A | 5/2000 | Koudijs | |
| 6,069,459 A | 5/2000 | Koudijs | |
| 6,071,748 A | 6/2000 | Modlin et al. | |
| 6,094,760 A | 8/2000 | Nonaka et al. | |
| 6,127,688 A | 10/2000 | Wu | |
| 6,152,599 A | 11/2000 | Salter | |
| 6,171,798 B1 | 1/2001 | Levine et al. | |
| 6,178,345 B1 | 1/2001 | Vilsmeier et al. | |
| 6,197,328 B1 | 3/2001 | Yanagawa | |
| 6,198,957 B1 | 3/2001 | Green | |
| 6,200,959 B1 | 3/2001 | Haynes et al. | |
| 6,204,510 B1 | 3/2001 | Ohkawa | |
| 6,207,400 B1 | 3/2001 | Kwon | |
| 6,218,675 B1 | 4/2001 | Akiyama et al. | |
| 6,222,905 B1 | 4/2001 | Yoda et al. | |
| 6,241,670 B1 | 6/2001 | Nambu | |
| 6,242,747 B1 | 6/2001 | Sugitani et al. | |
| 6,264,825 B1 | 7/2001 | Blackburn et al. | |
| 6,265,837 B1 | 7/2001 | Akiyama et al. | |
| 6,279,579 B1 | 8/2001 | Riaziat et al. | |
| 6,291,823 B1 | 9/2001 | Doyle et al. | |
| 6,316,776 B1 | 11/2001 | Hiramoto et al. | |
| 6,319,469 B1 | 11/2001 | Mian et al. | |
| 6,322,249 B1 | 11/2001 | Wofford et al. | |
| 6,331,194 B1 | 12/2001 | Sampayan et al. | |
| 6,345,114 B1 | 2/2002 | Mackie et al. | |
| 6,360,116 B1 | 3/2002 | Jackson, Jr. et al. | |
| 6,385,286 B1 | 5/2002 | Fitchard et al. | |
| 6,385,288 B1 | 5/2002 | Kanematsu | |
| 6,393,096 B1 | 5/2002 | Carol et al. | |
| 6,405,072 B1 | 6/2002 | Cosman | |
| 6,407,505 B1 | 6/2002 | Bertsche | |

| | | | | | | |
|---|---|---|---|---|---|---|
| 6,417,178 B1 | 7/2002 | Klunk et al. | 6,882,702 B2 | 4/2005 | Luo | |
| 6,424,856 B1 | 7/2002 | Vilsmeier et al. | 6,882,705 B2 | 4/2005 | Egley et al. | |
| 6,428,547 B1 | 8/2002 | Vilsmeier et al. | 6,888,326 B2 | 5/2005 | Amaldi et al. | |
| 6,433,349 B2 | 8/2002 | Akiyama et al. | 6,889,695 B2 | 5/2005 | Pankratov et al. | |
| 6,438,202 B1 | 8/2002 | Olivera et al. | 6,907,282 B2 | 6/2005 | Siochi | |
| 6,455,844 B1 | 9/2002 | Meyer | 6,922,455 B2 | 7/2005 | Jurczyk et al. | |
| 6,462,490 B1 | 10/2002 | Matsuda et al. | 6,929,398 B1 | 8/2005 | Tybinkowski et al. | |
| 6,465,957 B1 | 10/2002 | Whitham et al. | 6,936,832 B2 | 8/2005 | Norimine et al. | |
| 6,466,644 B1 | 10/2002 | Hughes et al. | 6,955,464 B1 | 10/2005 | Tybinkowski et al. | |
| 6,469,058 B1 | 10/2002 | Grove et al. | 6,963,171 B2 | 11/2005 | Sagawa et al. | |
| 6,472,834 B2 | 10/2002 | Hiramoto et al. | 6,963,771 B2 * | 11/2005 | Scarantino et al. | 600/436 |
| 6,473,490 B1 | 10/2002 | Siochi | 6,974,254 B2 | 12/2005 | Paliwal et al. | |
| 6,475,994 B2 | 11/2002 | Tomalia et al. | 6,984,835 B2 | 1/2006 | Harada | |
| 6,482,604 B2 | 11/2002 | Kwon | 6,990,167 B2 | 1/2006 | Chen | |
| 6,484,144 B2 | 11/2002 | Martin et al. | 7,015,490 B2 | 3/2006 | Wang et al. | |
| 6,487,274 B2 | 11/2002 | Bertsche | 7,046,762 B2 | 5/2006 | Lee | |
| 6,493,424 B2 | 12/2002 | Whitham | 7,051,605 B2 | 5/2006 | Lagraff et al. | |
| 6,497,358 B1 | 12/2002 | Walsh | 7,060,997 B2 | 6/2006 | Norimine et al. | |
| 6,498,011 B2 | 12/2002 | Hohn et al. | 7,077,569 B1 | 7/2006 | Tybinkowski et al. | |
| 6,500,343 B2 | 12/2002 | Siddiqi | 7,081,619 B2 | 7/2006 | Bashkirov et al. | |
| 6,504,899 B2 | 1/2003 | Pugachev et al. | 7,084,410 B2 | 8/2006 | Beloussov et al. | |
| 6,510,199 B1 | 1/2003 | Hughes et al. | 7,087,200 B2 | 8/2006 | Taboas et al. | |
| 6,512,942 B1 | 1/2003 | Burdette et al. | 7,112,924 B2 | 9/2006 | Hanna | |
| 6,516,046 B1 | 2/2003 | Frohlich et al. | 7,130,372 B2 | 10/2006 | Kusch et al. | |
| 6,527,443 B1 | 3/2003 | Vilsmeier et al. | 7,154,991 B2 | 12/2006 | Earnst et al. | |
| 6,531,449 B2 | 3/2003 | Khojasteh et al. | 7,186,986 B2 | 3/2007 | Hinderer et al. | |
| 6,535,837 B1 | 3/2003 | Schach Von Wittenau | 7,186,991 B2 | 3/2007 | Kato et al. | |
| 6,552,338 B1 | 4/2003 | Doyle | 7,203,272 B2 | 4/2007 | Chen | |
| 6,558,961 B1 | 5/2003 | Sarphie et al. | 7,209,547 B2 | 4/2007 | Baier et al. | |
| 6,560,311 B1 | 5/2003 | Shepard et al. | 7,221,733 B1 | 5/2007 | Takai et al. | |
| 6,562,376 B2 | 5/2003 | Hooper et al. | 7,252,307 B2 | 8/2007 | Kanbe et al. | |
| 6,584,174 B2 | 6/2003 | Schubert et al. | 7,257,196 B2 | 8/2007 | Brown et al. | |
| 6,586,409 B1 | 7/2003 | Wheeler | 7,391,026 B2 | 6/2008 | Trinkaus et al. | |
| 6,605,297 B2 | 8/2003 | Nadachi et al. | 2002/0007918 A1 | 1/2002 | Owen et al. | |
| 6,611,700 B1 | 8/2003 | Vilsmeier et al. | 2002/0077545 A1 | 6/2002 | Takahashi et al. | |
| 6,617,768 B1 | 9/2003 | Hansen | 2002/0080915 A1 | 6/2002 | Frohlich | |
| 6,618,467 B1 | 9/2003 | Ruchala et al. | 2002/0085668 A1 | 7/2002 | Blumhofer et al. | |
| 6,621,889 B1 | 9/2003 | Mostafavi | 2002/0091314 A1 | 7/2002 | Schlossbauer et al. | |
| 6,633,686 B1 | 10/2003 | Bakircioglu et al. | 2002/0115923 A1 | 8/2002 | Erbel | |
| 6,634,790 B1 | 10/2003 | Salter, Jr. | 2002/0120986 A1 | 9/2002 | Erbel et al. | |
| 6,636,622 B2 | 10/2003 | Mackie et al. | 2002/0122530 A1 | 9/2002 | Erbel et al. | |
| 6,637,056 B1 | 10/2003 | Tybinkowski et al. | 2002/0136439 A1 | 9/2002 | Ruchala et al. | |
| 6,646,383 B2 | 11/2003 | Bertsche et al. | 2002/0150207 A1 | 10/2002 | Kapatoes et al. | |
| 6,653,547 B2 | 11/2003 | Akamatsu | 2002/0187502 A1 | 12/2002 | Waterman et al. | |
| 6,661,870 B2 | 12/2003 | Kapatoes et al. | 2002/0193685 A1 | 12/2002 | Mate et al. | |
| 6,688,187 B1 | 2/2004 | Masquelier | 2003/0007601 A1 | 1/2003 | Jaffray et al. | |
| 6,690,965 B1 | 2/2004 | Riaziat et al. | 2003/0031298 A1 | 2/2003 | Xing | |
| 6,697,452 B2 | 2/2004 | Xing | 2003/0086527 A1 | 5/2003 | Speiser et al. | |
| 6,705,984 B1 | 3/2004 | Angha | 2003/0105650 A1 | 6/2003 | Lombardo et al. | |
| 6,713,668 B2 | 3/2004 | Akamatsu | 2003/0174872 A1 | 9/2003 | Chalana et al. | |
| 6,713,976 B1 | 3/2004 | Zumoto et al. | 2004/0010418 A1 | 1/2004 | Buonocore et al. | |
| 6,714,620 B2 | 3/2004 | Caflisch et al. | 2004/0068182 A1 * | 4/2004 | Misra | 600/427 |
| 6,714,629 B2 | 3/2004 | Vilsmeier | 2004/0116804 A1 | 6/2004 | Mostafavi | |
| 6,716,162 B2 | 4/2004 | Hakamata | 2004/0165696 A1 | 8/2004 | Lee | |
| 6,723,334 B1 | 4/2004 | McGee et al. | 2004/0202280 A1 | 10/2004 | Besson | |
| 6,741,674 B2 | 5/2004 | Lee | 2004/0230115 A1 | 11/2004 | Scarantino et al. | |
| 6,760,402 B2 | 7/2004 | Ghelmansarai | 2004/0254492 A1 | 12/2004 | Zhang et al. | |
| 6,774,383 B2 | 8/2004 | Norimine et al. | 2004/0254773 A1 | 12/2004 | Zhang et al. | |
| 6,787,771 B2 | 9/2004 | Bashkirov et al. | 2004/0264640 A1 | 12/2004 | Myles | |
| 6,787,983 B2 | 9/2004 | Yamanobe et al. | 2005/0013406 A1 | 1/2005 | Dyk et al. | |
| 6,788,764 B2 | 9/2004 | Saladin et al. | 2005/0031181 A1 | 2/2005 | Bi et al. | |
| 6,792,073 B2 | 9/2004 | Deasy et al. | 2005/0080332 A1 | 4/2005 | Shiu et al. | |
| 6,796,164 B2 | 9/2004 | McLoughlin et al. | 2005/0096515 A1 | 5/2005 | Geng | |
| 6,800,866 B2 | 10/2004 | Amemiya et al. | 2005/0123092 A1 | 6/2005 | Mistretta et al. | |
| 6,822,244 B2 | 11/2004 | Beloussov et al. | 2005/0143965 A1 * | 6/2005 | Failla et al. | 703/2 |
| 6,822,247 B2 | 11/2004 | Sasaki | 2005/0180544 A1 | 8/2005 | Sauer et al. | |
| 6,838,676 B1 | 1/2005 | Jackson | 2005/0197564 A1 | 9/2005 | Dempsey | |
| 6,842,502 B2 | 1/2005 | Jaffray et al. | 2005/0251029 A1 | 11/2005 | Khamene et al. | |
| 6,844,689 B1 | 1/2005 | Brown et al. | 2006/0074292 A1 | 4/2006 | Thomson et al. | |
| 6,871,171 B1 | 3/2005 | Agur et al. | 2006/0083349 A1 | 4/2006 | Harari et al. | |
| 6,873,115 B2 | 3/2005 | Sagawa et al. | 2006/0100738 A1 | 5/2006 | Alsafadi et al. | |
| 6,873,123 B2 | 3/2005 | Marchand et al. | 2006/0133568 A1 | 6/2006 | Moore | |
| 6,878,951 B2 | 4/2005 | Ma | 2006/0193429 A1 | 8/2006 | Chen | |

| | | | |
|---|---|---|---|
| 2006/0193441 A1 | 8/2006 | Cadman | |
| 2006/0285639 A1 | 12/2006 | Olivera et al. | |
| 2007/0041494 A1 | 2/2007 | Ruchala et al. | |
| 2007/0041495 A1 | 2/2007 | Olivera et al. | |
| 2007/0041497 A1 | 2/2007 | Schnarr et al. | |
| 2007/0041498 A1 | 2/2007 | Olivera et al. | |
| 2007/0041499 A1 | 2/2007 | Lu et al. | |
| 2007/0041500 A1 | 2/2007 | Olivera et al. | |
| 2007/0043286 A1 | 2/2007 | Lu et al. | |
| 2007/0076846 A1 | 4/2007 | Ruchala et al. | |
| 2007/0088573 A1 | 4/2007 | Ruchala et al. | |
| 2007/0104316 A1 | 5/2007 | Ruchala et al. | |
| 2007/0127623 A1 | 6/2007 | Goldman et al. | |
| 2007/0189591 A1 | 8/2007 | Lu et al. | |
| 2007/0195922 A1 | 8/2007 | Mackie et al. | |
| 2007/0195929 A1 | 8/2007 | Ruchala et al. | |
| 2007/0195930 A1 | 8/2007 | Kapatoes et al. | |
| 2007/0201613 A1 | 8/2007 | Lu et al. | |
| 2007/0211857 A1 | 9/2007 | Urano et al. | |

FOREIGN PATENT DOCUMENTS

| | | |
|---|---|---|
| CA | 2180227 | 12/1996 |
| WO | 03/076003 | 9/2003 |
| WO | 2004057515 | 7/2004 |

OTHER PUBLICATIONS

Ronald D. Rogus et al., "Accuracy of a Photogrammetry-Based Patient Positioning and Monitoring System for Radiation Therapy," Medical Physics, vol. 26, Issue 5, May 1999.

Yuan-Nan Young, "Registraion-Based Morphing of Active Contours for Segmentation of CT Scans," Mathematical Biosciences and Engineering, vol. 2, No. 1, Jan. 2005.

Anthony Yezzi et al., "A Variational Framework for Joint Segmentation and Registration," Mathematical Method in Biomedical Image Analysis, 2001. (Note: the title of the periodical and the date listed are from the International Search Report, however they do not appear on the article itself.).

Marcelo Bertalmio, et al., "Morphing Active Contours", IEEE Transactions on Pattern Analysis and Machine Intelligence, vol. 22, No. 7, pp. 733-737, Jul. 2000.

Lu, W., et al., "Automatic Re-Contouring in 4D Radiotherapy", Physical Medical Biology, Mar. 7, 2006, 51(5): 1077-99.

Lu, W., et al., 2004 Automatic Re-Contouring for 4-D Planning and Adaptive Radiotherapy, The 90th RSNA Meeting, Chicago, Illinois, (abstract: Radiology 227 (p.) 543).

Lu, W., et al., 2004 Automatic Re-Contouring Regions of Interest Based on Deformable Registration and Surface Reconstruction, AAPM 2004, (abstract: Medical Physics 31, 1845-6).

Ruchala, Kenneth, et al., "Adaptive IMRT with Tomotherapy", RT Image, vol. 14, No. 25, pp. 14-18, Jun. 18, 2001.

* cited by examiner

METHOD OF AND SYSTEM FOR PREDICTING DOSE DELIVERY

RELATED APPLICATIONS

This application claims priority to U.S. Provisional Patent Application No. 60/701,580, filed on Jul. 22, 2005, titled SYSTEM AND METHOD FOR FEEDBACK GUIDED QUALITY ASSURANCE AND ADAPTATIONS TO RADIATION THERAPY TREATMENT, the entire contents of which are incorporated herein by reference.

BACKGROUND

Over the past decades improvements in computers and networking, radiation therapy treatment planning software, and medical imaging modalities (CT, MRI, US, and PET) have been incorporated into radiation therapy practice. These improvements have led to the development of image guided radiation therapy ("IGRT"). IGRT is radiation therapy that uses cross-sectional images of the patient's internal anatomy to better target the radiation dose in the tumor while reducing the radiation exposure to healthy organs. The radiation dose delivered to the tumor is controlled with intensity modulated radiation therapy ("IMRT"), which involves changing the size, shape, and intensity of the radiation beam to conform to the size, shape, and location of the patient's tumor. IGRT and IMRT lead to improved control of the tumor while simultaneously reducing the potential for acute side effects due to irradiation of healthy tissue surrounding the tumor.

IMRT is becoming the standard of care in several countries. However, in many situations, IMRT is not used to treat a patient due to time, resources, and billing constraints. Daily images of the patient can be used to guarantee that the high gradients generated by IMRT plans are located on the correct position for patient treatment. Also these images can provide necessary information to adapt the plan online or offline if needed.

It is commonly known in the field of radiation therapy that there are many sources of uncertainty and change that can occur during a course of a patient's treatment. Some of these sources represent random errors, such as small differences in a patient's setup position each day. Other sources are attributable to physiological changes, which might occur if a patient's tumor regresses or the patient loses weight during therapy. A third possible category regards motion. Motion can potentially overlap with either of the other categories, as some motion might be more random and unpredictable, such as a patient coughing or passing gas, whereas other motion can be more regular, such as breathing motion, sometimes.

SUMMARY

In radiation therapy, uncertainties can affect the quality of a patient's treatment. For example, when delivering a treatment dose to a target region, it is standard practice to also treat a high-dose "margin" region about the target. This helps ensure that the target receives the desired dose, even if its location changes during the course of the treatment, or even during a single fraction. The less definite a target's location, the larger the margins that typically need to be used.

Adaptive radiation therapy generally refers to the concept of using feedback during the course of radiation therapy treatment to improve future treatments. Feedback can be used in off-line adaptive therapy processes and on-line adaptive therapy processes. Off-line adaptive therapy processes occur while the patient is not being treated, such as in between treatment fractions. In one version of this, during each fraction, a new CT image of the patient is acquired before or after each of the fractions. After the images are acquired from the first few treatment fractions, the images are evaluated to determine an effective envelope of the multi-day locations of target structures. A new plan can then be developed to better reflect the range of motion of the target structure, rather than using canonical assumptions of motion. A more complex version of off-line adaptive therapy is to recalculate the delivered dose after each fraction and accumulate these doses, potentially utilizing deformation techniques, during this accumulation to account for internal motion. The accumulated dose can then be compared to the planned dose, and if any discrepancies are noted, subsequent fractions can be modified to account for the changes.

On-line adaptive therapy processes typically occur while the patient is in the treatment room, and potentially, but not necessarily, during a treatment delivery. For example, some radiation therapy treatment systems are equipped with imaging systems, such as on-line CT or X-Ray systems. These systems can be used prior to treatment to validate or adjust the patient's setup for the treatment delivery. The imaging systems may also be used to adapt the treatment during the actual treatment delivery. For example, an imaging system potentially can be used concurrently with treatment to modify the treatment delivery to reflect changes in patient anatomy.

One aspect of the present invention is to disclose new opportunities for the application of adaptive therapy techniques, and additional aspects are to present novel methods for adaptive therapy. In particular, adaptive therapy has typically focused on feedback to modify a patient's treatment, but the present invention focuses on adaptive therapy processes being used in a quality assurance context. This is particularly true in the context of whole-system verification.

For example, a detector can be used to collect information indicating how much treatment beam has passed through the patient, from which the magnitude of the treatment output can be determined as well as any radiation pattern that was used for the delivery. The benefit of this delivery verification process is that it enables the operator to detect errors in the machine delivery, such as an incorrect leaf pattern or machine output.

However, validating that the machine is functioning properly does not itself ensure proper delivery of a treatment plan, as one also needs to validate that the external inputs used to program the machine are effective and consistent. Thus, one aspect of the invention includes the broader concept of an adaptive-type feedback loop for improved quality assurance of the entire treatment process. In this aspect, the invention includes the steps of positioning the patient for treatment and using a method for image-guidance to determine the patient's position, repositioning the patient as necessary for treatment based upon the image-guidance, and beginning treatment. Then, either during or after treatment, recalculating the patient dose and incorporating the patient image information that had been collected before or during treatment. After completion of these steps, quality assurance data is collected to analyze the extent to which the delivery was not only performed as planned, but to validate that the planned delivery is reasonable in the context of the newly available data. In this regard, the concept of feedback is no longer being used to indicate changes to the treatment based on changes in the patient or delivery, but to validate the original delivery itself.

As an example, it is possible that a treatment plan might be developed for a patient, but that the image used for planning became corrupted, such as by applying an incorrect density calibration. In this case, the treatment plan will be based upon incorrect information, and might not deliver the correct dose to the patient. Yet, many quality assurance techniques will not detect this error because they will verify that the machine is operating as instructed, rather than checking whether the instructions to the machine are based on correct input information. Likewise, some adaptive therapy techniques could be applied to this delivery, but if the calibration problem of this example persisted, then the adapted treatments would suffer from similar flaws.

There are a number of processes that can be used to expand the use of feedback for quality assurance purposes. For example, in one embodiment, this process would include the delivery verification techniques described above. The validation of machine performance that these methods provide is a valuable component of a total-system quality assurance toolset. Moreover, the delivery verification processes can be expanded to analyze other system errors, such as deliveries based on images with a truncated field-of-view.

In one embodiment, the invention provides a method of predicting a radiation dose delivered to a patient in the delivery of a treatment plan to the patient, the patient having a profile. The method comprises the acts of generating a first image of at least a portion of the patient, defining a treatment plan for the patient, generating a second image of at least a portion of the patient while the patient is substantially in a treatment position, updating the patient profile with the second image, and predicting the radiation dose to be delivered to the patient based upon the patient profile and the treatment plan.

In another embodiment, the invention provides a method of determining a radiation dose to be delivered to a patient. The method comprises the acts of generating a treatment plan for the patient, acquiring an image of at least a portion of the patient while the patient is substantially in the treatment position, calculating a plurality of doses that would be delivered to the patient for each of a plurality of patient profiles, and selecting one of the patient profiles for delivery of the treatment plan.

In yet another embodiment, the invention provides a method of determining a radiation dose to be delivered to a patient. The method comprises the acts of delivering radiation to a patient according to a predetermined treatment plan, acquiring an image of at least a portion of the patient during delivery of the radiation, calculating a radiation dose during delivery of the radiation, the radiation dose based on at least in part on the acquired image, and determining whether to modify delivery of the radiation.

In another embodiment, the invention provides a method of determining a radiation dose to be delivered to a patient. The method comprises the acts of generating a treatment plan for the patient, the treatment plan including a first image, acquiring a second image of at least a portion of the patient, positioning the patient based on the second image, and predicting the radiation dose to be delivered to the patient based upon the first image and the patient position.

Other aspects of the invention will become apparent by consideration of the detailed description and accompanying drawings.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

Although directional references, such as upper, lower, downward, upward, rearward, bottom, front, rear, etc., may be made herein in describing the drawings, these references are made relative to the drawings (as normally viewed) for convenience. These directions are not intended to be taken literally or limit the present invention in any form. In addition, terms such as "first", "second", and "third" are used herein for purposes of description and are not intended to indicate or imply relative importance or significance.

In addition, it should be understood that embodiments of the invention include both hardware, software, and electronic components or modules that, for purposes of discussion, may be illustrated and described as if the majority of the components were implemented solely in hardware. However, one of ordinary skill in the art, and based on a reading of this detailed description, would recognize that, in at least one embodiment, the electronic based aspects of the invention may be implemented in software. As such, it should be noted that a plurality of hardware and software based devices, as well as a plurality of different structural components may be utilized to implement the invention. Furthermore, and as described in subsequent paragraphs, the specific mechanical configurations illustrated in the drawings are intended to exemplify embodiments of the invention and that other alternative mechanical configurations are possible.

Figure 1:
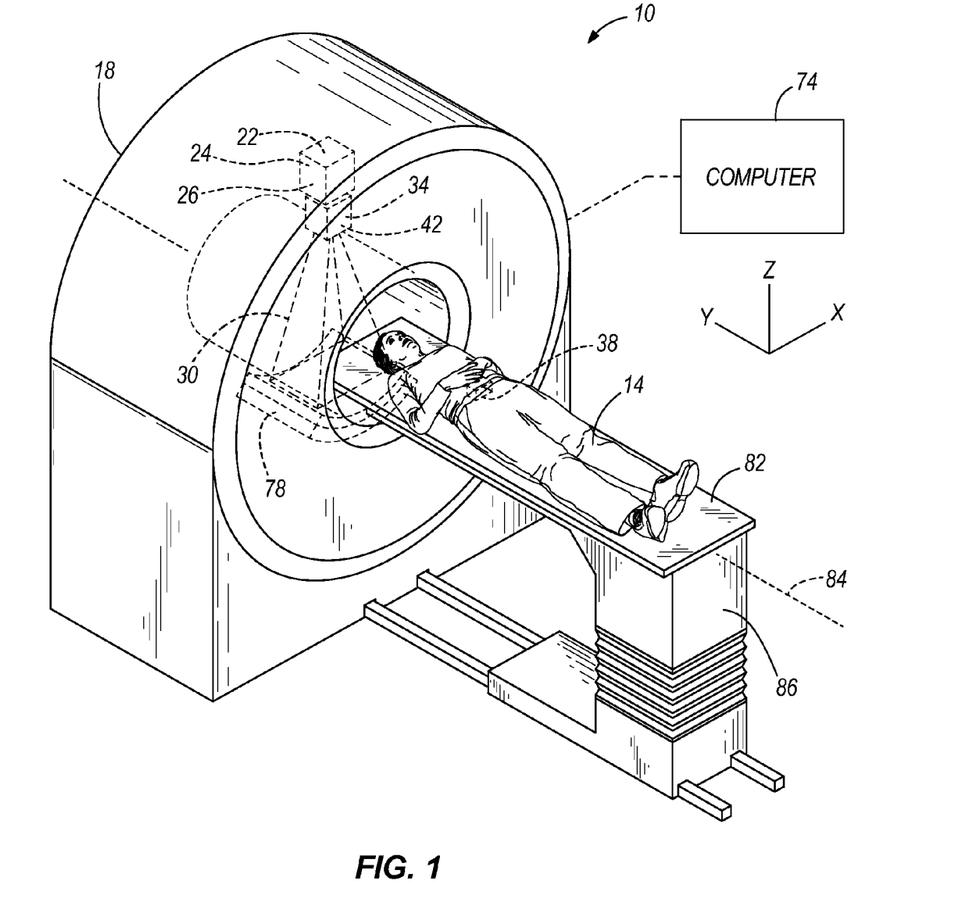
FIG. 1 is a perspective view of a radiation therapy treatment system.

FIG. 1 illustrates a radiation therapy treatment system 10 that can provide radiation therapy to a patient 14. The radiation therapy treatment can include photon-based radiation therapy, brachytherapy, electron beam therapy, proton, neutron, or particle therapy, or other types of treatment therapy. The radiation therapy treatment system 10 includes a gantry 18. The gantry 18 can support a radiation module 22, which can include a radiation source 24 and a linear accelerator 26 operable to generate a beam 30 of radiation. Though the gantry 18 shown in the drawings is a ring gantry, i.e., it extends through a full 360° arc to create a complete ring or circle, other types of mounting arrangements may also be employed. For example, a C-type, partial ring gantry, or robotic arm could be used. Any other framework capable of positioning the radiation module 22 at various rotational and/or axial positions relative to the patient 14 may also be employed. In addition, the radiation source 24 may travel in path that does not follow the shape of the gantry 18. For example, the radiation source 24 may travel in a non-circular path even though the illustrated gantry 18 is generally circular-shaped.

The radiation module 22 can also include a modulation device 34 operable to modify or modulate the radiation beam 30. The modulation device 34 provides the modulation of the radiation beam 30 and directs the radiation beam 30 toward the patient 14. Specifically, the radiation beam 34 is directed toward a portion of the patient. Broadly speaking, the portion may include the entire body, but is generally smaller than the entire body and can be defined by a two-dimensional area and/or a three-dimensional volume. A portion desired to receive the radiation, which may be referred to as a target 38 or target region, is an example of a region of interest. Another type of region of interest is a region at risk. If a portion includes a region at risk, the radiation beam is preferably diverted from the region at risk. The patient 14 may have more than one target region that needs to receive radiation therapy. Such modulation is sometimes referred to as intensity modulated radiation therapy ("IMRT").

Figure 2:
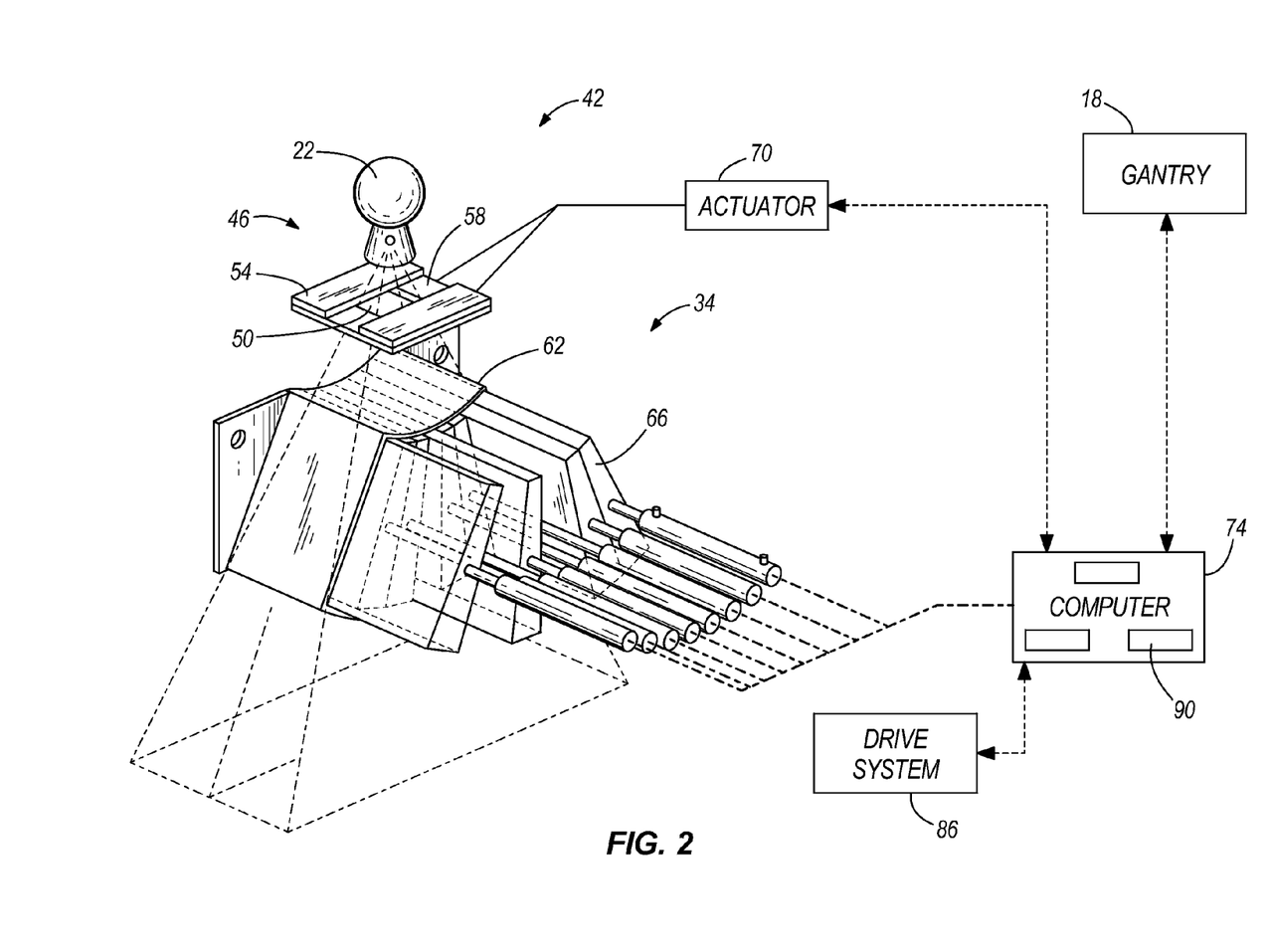
FIG. 2 is a perspective view of a multi-leaf collimator that can be used in the radiation therapy treatment system illustrated in FIG. 1.

The modulation device 34 can include a collimation device 42 as illustrated in FIG. 2. The collimation device 42 includes a set of jaws 46 that define and adjust the size of an aperture 50 through which the radiation beam 30 may pass. The jaws 46 include an upper jaw 54 and a lower jaw 58. The upper jaw 54 and the lower jaw 58 are moveable to adjust the size of the aperture 50.

In one embodiment, and illustrated in FIG. 2, the modulation device 34 can comprise a multi-leaf collimator 62, which includes a plurality of interlaced leaves 66 operable to move from position to position, to provide intensity modulation. It is also noted that the leaves 66 can be moved to a position anywhere between a minimally and maximally-open position. The plurality of interlaced leaves 66 modulate the strength, size, and shape of the radiation beam 30 before the radiation beam 30 reaches the target 38 on the patient 14. Each of the leaves 66 is independently controlled by an actuator 70, such as a motor or an air valve so that the leaf 66 can open and close quickly to permit or block the passage of radiation. The actuators 70 can be controlled by a computer 74 and/or controller.

The radiation therapy treatment system 10 can also include a detector 78, e.g., a kilovoltage or a megavoltage detector, operable to receive the radiation beam 30. The linear accelerator 26 and the detector 78 can also operate as a computed tomography (CT) system to generate CT images of the patient 14. The linear accelerator 26 emits the radiation beam 30 toward the target 38 in the patient 14. The target 38 absorbs some of the radiation. The detector 78 detects or measures the amount of radiation absorbed by the target 38. The detector 78 collects the absorption data from different angles as the linear accelerator 26 rotates around and emits radiation toward the patient 14. The collected absorption data is transmitted to the computer 74 to process the absorption data and to generate images of the patient's body tissues and organs. The images can also illustrate bone, soft tissues, and blood vessels.

The CT images can be acquired with a radiation beam 30 that has a fan-shaped geometry, a multi-slice geometry or a cone-beam geometry. In addition, the CT images can be acquired with the linear accelerator 26 delivering megavoltage energies or kilovoltage energies. It is also noted that the acquired CT images can be registered with previously acquired CT images (from the radiation therapy treatment system 10 or other image acquisition devices, such as other CT scanners, MRI systems, and PET systems). For example, the previously-acquired CT images for the patient 14 can include identified targets 38 made through a contouring process. The newly-acquired CT images for the patient 14 can be registered with the previously acquired CT images to assist in identifying the targets 38 in the new CT images. The registration process can use rigid or deformable registration tools.

In some embodiments, the radiation therapy treatment system 10 can include an x-ray source and a CT image detector. The x-ray source and the CT image detector operate in a similar manner as the linear accelerator 26 and the detector 78 as described above to acquire image data. The image data is transmitted to the computer 74 where it is processed to generate images of the patient's body tissues and organs.

The radiation therapy treatment system 10 can also include a patient support, such as a couch 82 (illustrated in FIG. 1), which supports the patient 14. The couch 82 moves along at least one axis 84 in the x, y, or z directions. In other embodiments of the invention, the patient support can be a device that is adapted to support any portion of the patient's body. The patient support 82 is not limited to having to support the entire patient's body. The system 10 also can include a drive system 86 operable to manipulate the position of the couch 82. The drive system 86 can be controlled by the computer 74.

Figure 3:
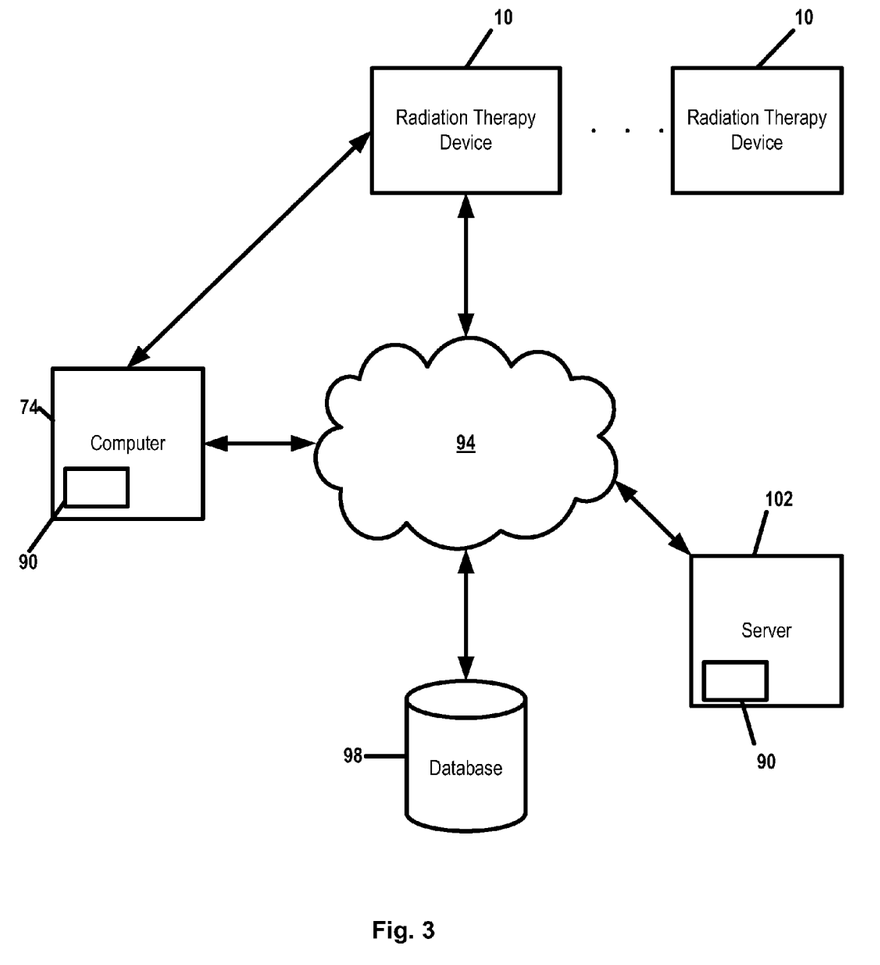
FIG. 3 is a schematic illustration of the radiation therapy treatment system of FIG. 1.

The computer 74, illustrated in FIGS. 2 and 3, includes an operating system for running various software programs and/or a communications application. In particular, the computer 74 can include a software program(s) 90 that operates to communicate with the radiation therapy treatment system 10. The software program(s) 90 is operable to receive data from external software programs and hardware and it is noted that data may be input to the software program(s) 90.

The computer 74 can include any suitable input/output device adapted to be accessed by medical personnel. The computer 74 can include typical hardware such as a processor, I/O interfaces, and storage devices or memory. The computer 74 can also include input devices such as a keyboard and a mouse. The computer 74 can further include standard output devices, such as a monitor. In addition, the computer 74 can include peripherals, such as a printer and a scanner.

The computer 74 can be networked with other computers 74 and radiation therapy treatment systems 10. The other computers 74 may include additional and/or different computer programs and software and are not required to be identical to the computer 74, described herein. The computers 74 and radiation therapy treatment system 10 can communicate with a network 94. The computers 74 and radiation therapy treatment systems 10 can also communicate with a database(s) 98 and a server(s) 102. It is noted that the software program(s) 90 could also reside on the server(s) 102.

The network 94 can be built according to any networking technology or topology or combinations of technologies and topologies and can include multiple sub-networks. Connections between the computers and systems shown in FIG. 3 can be made through local area networks ("LANs"), wide area networks ("WANs"), public switched telephone networks ("PSTNs"), wireless networks, Intranets, the Internet, or any other suitable networks. In a hospital or medical care facility, communication between the computers and systems shown in FIG. 3 can be made through the Health Level Seven ("HL7") protocol or other protocols with any version and/or other required protocol. HL7 is a standard protocol which specifies the implementation of interfaces between two computer applications (sender and receiver) from different vendors for electronic data exchange in health care environments. HL7 can allow health care institutions to exchange key sets of data from different application systems. Specifically, HL7 can define the data to be exchanged, the timing of the interchange, and the communication of errors to the application. The formats are generally generic in nature and can be configured to meet the needs of the applications involved.

Communication between the computers and systems shown in FIG. 3 can also occur through the Digital Imaging and Communications in Medicine ("DICOM") protocol with any version and/or other required protocol. DICOM is an international communications standard developed by NEMA that defines the format used to transfer medical image-related data between different pieces of medical equipment. DICOM RT refers to the standards that are specific to radiation therapy data.

The two-way arrows in FIG. 3 generally represent two-way communication and information transfer between the network 94 and any one of the computers 74 and the systems 10 shown in FIG. 3. However, for some medical and computerized equipment, only one-way communication and information transfer may be necessary.

Figure 4:
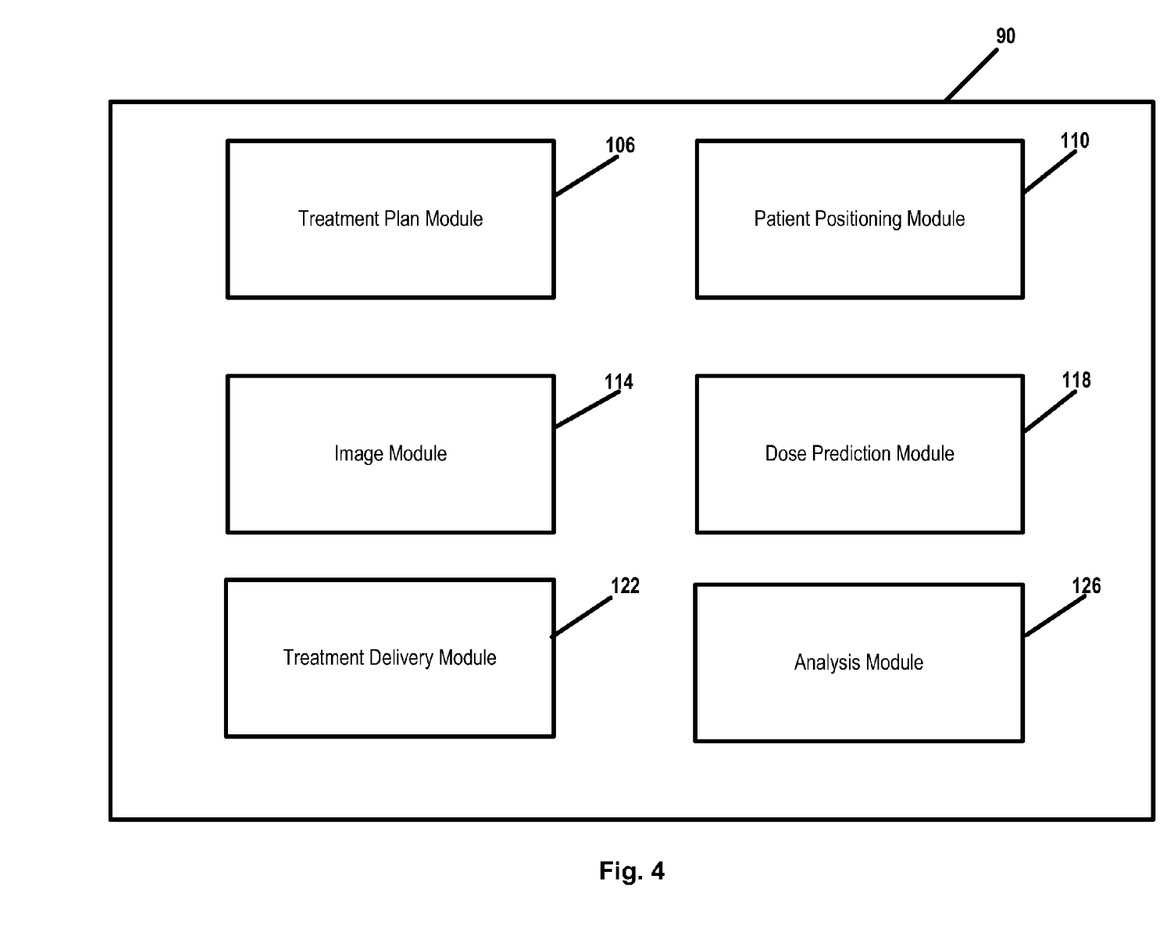
FIG. 4 is a schematic diagram of a software program used in the radiation therapy treatment system of a method of evaluating the delivery of a treatment plan according to one embodiment of the present invention.

The software program 90 includes a plurality of modules illustrated in FIG. 4 that communicate with one another to perform functions of the radiation therapy treatment process. The various modules communication with one another to predict a radiation dose to be delivered to the patient before a treatment is commenced. The various modules also communicate with one another to determine a radiation dose being delivered to the patient during delivery of a treatment plan. The various modules also communicate with one another to determine the radiation dose delivered to the patient. It is noted that not all of the modules discussed below are needed to communicate and to carry out the various functions mentioned above.

The software program 90 includes a treatment plan module 106 operable to generate a treatment plan for the patient 14 based on data input to the system 10 by medical personnel. The data includes one or more images (e.g., planning images and/or pre-treatment images) of at least a portion of the patient 14. The treatment plan module 106 separates the treatment into a plurality of fractions and determines the radiation dose for each fraction or treatment based on the prescription input by medical personnel. The treatment plan module 106 also determines the radiation dose for the target 38 based on various contours drawn around the target 38. Multiple targets 38 may be present and included in the same treatment plan.

The software program 90 also includes a patient positioning module 110 operable to position and align the patient 14 with respect to the isocenter of the gantry 18 for a particular treatment fraction. While the patient is on the couch 82, the patient positioning module 110 acquires an image of the patient 14 and compares the current position of the patient 14 to the position of the patient in a planning image. If the patient's position needs to be adjusted, the patient positioning module 110 provides instructions to the drive system 86 to move the couch 82 or the patient 14 can be manually moved to the new position. In one construction, the patient positioning module 110 can receive data from lasers positioned in the treatment room to provide patient position data with respect to the isocenter of the gantry 18. Based on the data from the lasers, the patient positioning module 110 provides instructions to the drive system 86, which moves the couch 82 to achieve proper alignment of the patient 14 with respect to the gantry 18. It is noted that devices and systems, other than lasers, can be used to provide data to the patient positioning module 110 to assist in the alignment process.

The software program 90 also includes an image module 114 operable to acquire images of at least a portion of the patient 14. The image module 114 can instruct the on-board image device, such as a CT imaging device to acquire images of the patient 14 before treatment commences, during treatment, and after treatment according to desired protocols. Other off-line imaging devices or systems may be used to acquire pre-treatment images of the patient 14, such as non-quantitative CT, MRI, PET, SPECT, ultrasound, transmission imaging, fluoroscopy, RF-based localization, and the like. The acquired images can be used for registration of the patient 14 and/or to determine or predict a radiation dose to be delivered to the patient 14. The acquired images also can be used to determine a radiation dose that the patient 14 received during the prior treatments. The image module 114 also is operable to acquire images of at least a portion of the patient 14 while the patient is receiving treatment to determine a radiation dose that the patient 14 is receiving in real-time (discussed below).

The software program 90 also includes a radiation dose prediction module 118 operable to predict a radiation dose to be delivered to the patient 14 before a radiation treatment is delivered. The dose prediction module 118 can determine the effect that the location and/or movement of the patient and/or changes in anatomy will have on the delivery of the prescribed radiation dose.

The dose prediction module 118 is operable to receive patient data (real-time and historic), patient images (e.g., the planning images and/or the pre-treatment images), patient position (e.g., actual or intended position) data, motion data, anatomical position data, and system or machine data. Some or all of this data may define the patient profile. The dose prediction module 118 can calculate the radiation dose that is to be delivered to the patient based on some or all of the data in the patient profile. The dose prediction module 118 also is operable to compare the predicted radiation dose to the scheduled radiation dose about to be delivered to the patient 14 to verify that the scheduled radiation dose is not impacted by any changes in the patient's anatomy that may have occurred since the treatment plan was generated. The comparison can assist the medical personnel in determining if the patient position needs to be adjusted, the radiation dose needs to be adjusted, the machine settings need to be adjusted, and whether other adjustments need to be made prior to delivery of the treatment plan.

In some constructions, the dose prediction module 118 can utilize deformable registration to generate the dose prediction. Registration is a method for determining the correlation between locations of a patient's anatomy or physiology across multiple images. Deformable registration is a method of determining the correlation between locations of a patient's anatomy or physiology to account for non-rigid changes in anatomy between the images, phases, or times. When using deformable registration to predict the dose to be delivered to the patient 14, the predicted dose can take into consideration the accumulated radiation dose, i.e., radiation doses that the patient 14 has received from prior treatments.

When using deformable registration to generate dose prediction, the dose prediction module 118 can transform a contour(s) of a patient structure. Generally, a contour(s) is defined for planning purposes, but in this embodiment, the dose prediction module 118 can modify the contour(s) based on the dose prediction, patient data, images, and/or changes in patient data throughout the treatment process. Rather than require an operator to manually contour the image, it can be both faster and more consistent to perform a deformable image registration, and then use the deformation results as the basis for modifying the original contour set to reflect the new patient anatomy.

A benefit of the dose prediction module 118 identifying a contour(s) using deformable registration techniques is that the contours generated can provide a validation of the deformation process. If the generated contours closely reflect contours that one would manually draw, then it is a good indication that the deformation process is reasonable; whereas if the automatic contours are less relevant, it indicates to the medical personnel that perhaps the deformation is inappropriate, but also provides the medical personnel an opportunity to verify the manual contours to check for mistakes or inconsistencies.

The dose prediction module 118 can provide information to the medical personnel related to the biological effect that the predicted radiation dose has on the patient 14. The dose prediction module 118 can determine the biological effects of radiation on tissues, tumors, and organs based on the predicted radiation dose that the patient 14 is going to receive and/or the patient's registration. Based on the biological effects, the medical personnel can adjust the patient 14, the system settings, or make other adjustments in the treatment plan. The biological information can be incorporated in the patient registration process to identify a preferred position for the patient 14 that results in a delivered dose with a preferred biological effect.

In one example, the dose prediction module 118 also is operable to calculate the predicted radiation dose based on the pre-treatment image(s), which is acquired just prior to delivery of the treatment plan to register the patient 14, to evaluate whether the predicted radiation dose is acceptable. If the predicted radiation dose is not acceptable, the medical personnel can make the necessary adjustments to the patient location and/or the system settings until the radiation dose is acceptable. If the pre-treatment image is not ideal for dose calculation, the pre-treatment image can be used for registration and the radiation dose can be recalculated on a different image (e.g., the planning image) incorporating the registration specified. This latter use of the pre-treatment image to calculate predicted radiation dose can assess some effects of how registration may affect the radiation dose distribution.

The dose prediction module 118 also is operable to calculate a predicted radiation dose for a plurality of registration positions. The patient 14 can be moved into various positions and the dose prediction module 118 can calculate the predicted radiation dose for each of the positions based on some or all of the patient data (real-time and historic), patient images (e.g., the planning images and/or the pre-treatment images), patient position data, anatomical position data, and system or machine data. The medical personnel can select one of the positions for the patient 14 based on the calculated predicted radiation dose, which is based upon the actual dose that would be delivered, rather than on an image registration or an alignment of the pre-treatment image with a dose calculation that was based upon a different image (e.g., the planning image).

The software program 90 also includes a treatment delivery module 122 operable to instruct the radiation therapy treatment system 10 to deliver the treatment plan to the patient 14 according to the treatment plan. The treatment delivery module 122 can generate and transmit instructions to the gantry 18, the linear accelerator 26, the modulation device 34, and the couch drive system 86 to deliver radiation to the patient 14. The instructions coordinate the necessary movements of the gantry 18, the modulation device 34, and the couch drive system 86 to deliver the radiation beam 30 to the proper target in the proper amount as specified in the treatment plan.

The treatment delivery module 122 also calculates the appropriate pattern, position, and intensity of the radiation beam 30 to be delivered, to match the prescription as specified by the treatment plan. The pattern of the radiation beam 30 is generated by the modulation device 34, and more particularly by movement of the plurality of leaves in the multi-leaf collimator. The treatment delivery module 122 can utilize canonical, predetermined or template leaf patterns to generate the appropriate pattern for the radiation beam 30 based on the treatment parameters.

The software program 90 also includes an analysis module 126 operable to receive and analyze data from any of the modules 110, 114, 118, and 122, the system 10, and other data to determine the effect that patient movement or other changes have on treatment delivery. For example, the analysis module 126 can collect data during delivery of the treatment plan and compare the predicted radiation dose to the actual dose delivered to the patient 14. The analysis module 126 can receive data from the image module 114 and dose prediction module 118, and while treatment is being delivered, analyze the change in radiation dose that the patient 14 receives as a result of patient movement during the treatment. In this example, the image module 114 can acquire images of at least a portion of the patient 14 while treatment is being delivered. The image module 114 can be set to automatically take images at certain intervals or can receive instructions to take images as needed from the medical personnel. Based upon this information (e.g., change in radiation dose delivered to the patient 14) or new dose calculation, the medical personnel can opt to adjust the patient 14 or system settings or discontinue the treatment. If any adjustments are desired, the adjustments can be made during treatment delivery.

The analysis module 126 can evaluate the effect(s) of any patient change during treatment on treatment delivery. The analysis module 126 can utilize system data and/or patient location data to generate a running predicted dose during the course of the treatment. The running predicted dose can be generated in real time as the treatment delivery progresses to determine whether adjustments need to be made to the system or the patient 14 and/or to continue or pause the treatment delivery. The analysis module 126 can utilize system and patient feedback to continuously or periodically (as instructed by the medical personnel) update the running predicted dose, which can occur in real time during the treatment delivery.

The analysis module 126 can use the dose prediction data to analyze other ways in which the patient 14 may have been preferably set up for delivery of the treatment. The patient 14 and the medical personnel can benefit by reducing the amount of time for set up for future fractions of the treatment. The analysis module 126 can determine whether the position of the patient 14 and the system settings should be changed for subsequent treatments. The analysis module 126 also can identify where and how the changes should be made (e.g., changing the system settings and/or repositioning the patient 14).

The analysis module 126 can utilize data related to the dose actually delivered and the biological effects of the radiation dose delivered to generate a biological model that relates the clinical dose to the patient effect. The net radiation dose delivered (accumulated using deformation techniques) can be used to estimate the biological effect that would result from continuing the treatment, and likewise, possible alternatives for adapting the treatment would be evaluated for a preferred biological effect. The resulting fractionation schedule, dose distribution, and plans can reflect this culmination of information.

Figure 5:
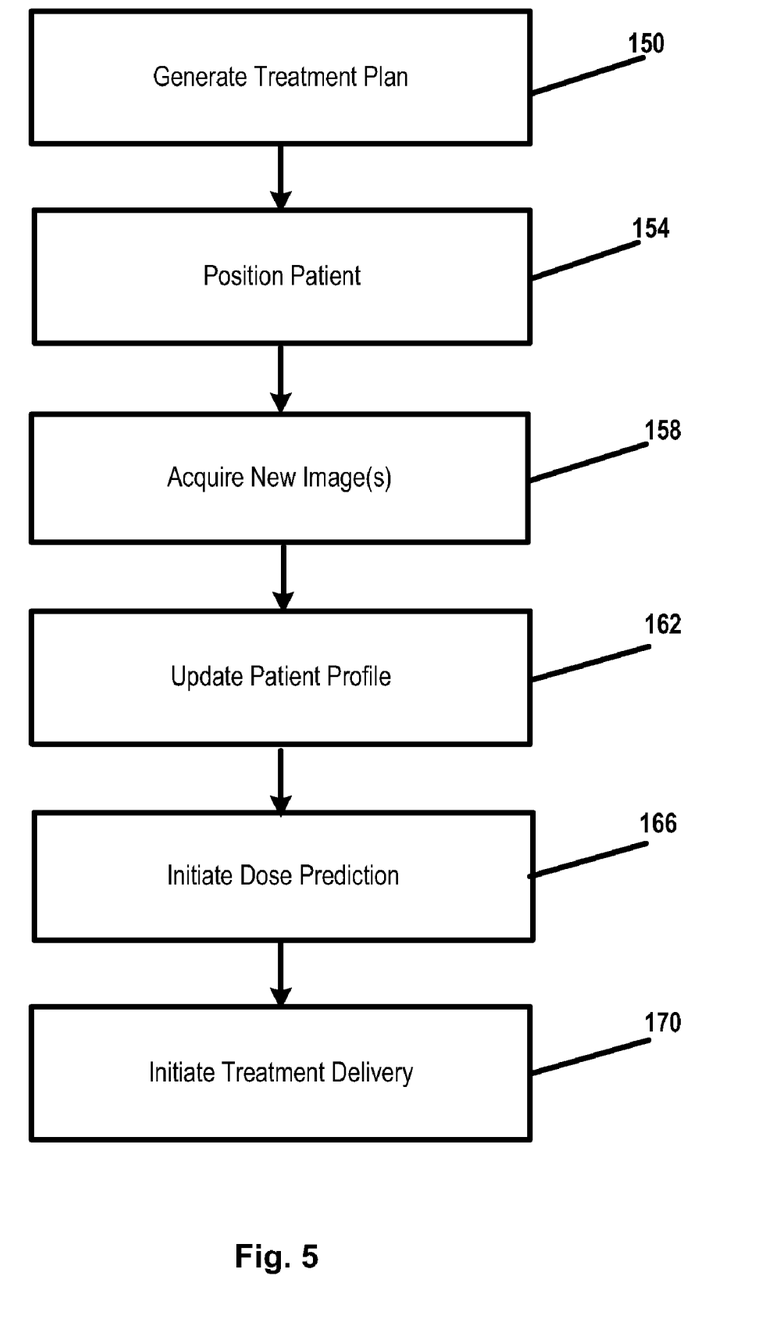
FIG. 5 is a flow chart of a method of predicting a radiation dose to be delivered to a patient according to one embodiment of the present invention.

FIG. 5 illustrates a flow chart of a method of predicting a radiation dose to be delivered to a patient. Medical personnel generate (at 150) a treatment plan for the patient 14 based on patient data, images, or other information. When the patient 14 is ready for a treatment, medical personnel position (at 154) the patient 14 substantially in the treatment position, on the couch 82, with the assistance of the patient positioning module 110 prior to delivery of treatment. While the patient 14 is in the position, the image module 114 acquires (at 158) a new image of the patient 14, which can assist in proper positioning of the patient 14. Additional positioning adjustments can be made as necessary. The dose prediction module 118 receives the image data and updates (at 162) the patient profile. The medical personnel initiates (at 166) the generation of a radiation dose prediction with the dose prediction module 118. Based on the dose prediction, the patient 14 and/or system settings can be adjusted. After readjustments (if necessary), the medical personnel initiates (at 170) treatment according to the treatment plan with the assistance of the treatment delivery module 122.

Figure 6:
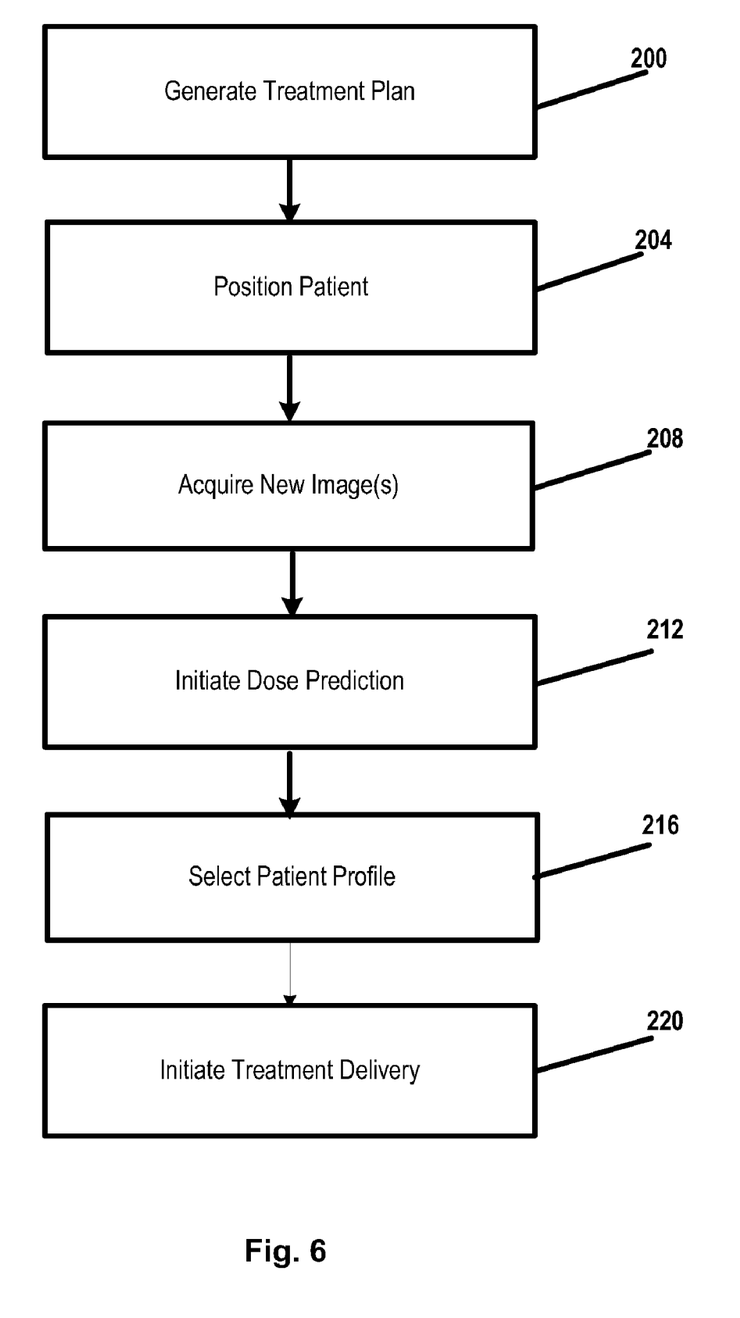
FIG. 6 is a flow chart of a method of predicting a radiation dose to be delivered to a patient according to one embodiment of the present invention.

FIG. 6 illustrates a flow chart of a method of predicting a radiation dose to be delivered to a patient. Medical personnel generate (at 200) a treatment plan for the patient 14 based on patient data, images, or other information. When the patient 14 is ready for a treatment, medical personnel position (at 204) the patient 14 substantially in the treatment position, on the couch 82, with the assistance of the patient positioning module 110 prior to delivery of treatment. While the patient 14 is in the position, the image module 114 acquires (at 208) a new image of the patient 14, which can assist in proper positioning of the patient 14. Additional positioning adjustments can be made as necessary. The medical personnel initiates (at 212), using the dose prediction module 118, the generation of a plurality of radiation doses that would be delivered to the patient 14 for each of a plurality of patient profiles. The patient profiles can include different data such that the medical personnel selects (at 216) the patient profile to be used for treatment delivery based on the desired radiation dose to be delivered to the patient. After selection of the patient profile, the medical personnel initiates (at 220) delivery of the treatment with the assistance of the treatment delivery module 122.

Figure 7:
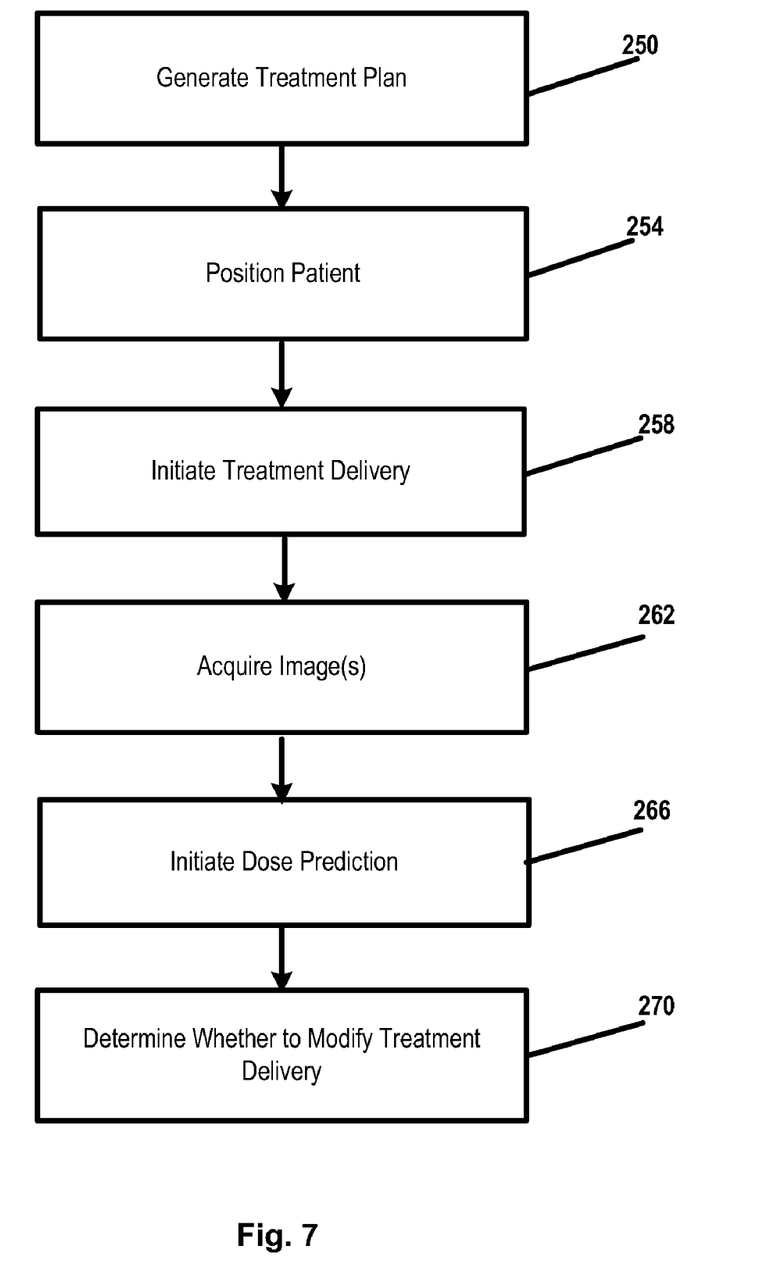
FIG. 7 is a flow chart of a method of predicting a radiation dose to be delivered to a patient according to one embodiment of the present invention.

FIG. 7 illustrates a flow chart of a method of predicting a radiation dose to be delivered to a patient. Medical personnel generate (at 250) a treatment plan for the patient 14 based on patient data, images, or other information. When the patient 14 is ready for a treatment, medical personnel position (at 254) the patient 14 substantially in the treatment position, on the couch 82, with the assistance of the patient positioning module 110 prior to delivery of treatment. The medical personnel initiates (at 258) delivery of the treatment plan with the assistance of the treatment delivery module 122. During delivery of the treatment plan, the image module 114 acquires (at 262) an image of the patient 14. The medical personnel initiates (at 266), using the dose prediction module 118, the generation of a radiation dose prediction, which is based in part on the newly-acquired image of the patient 14. Based on the calculated radiation dose, the medical personnel determines (at 270) whether delivery of the treatment needs to be modified.

Figure 8:
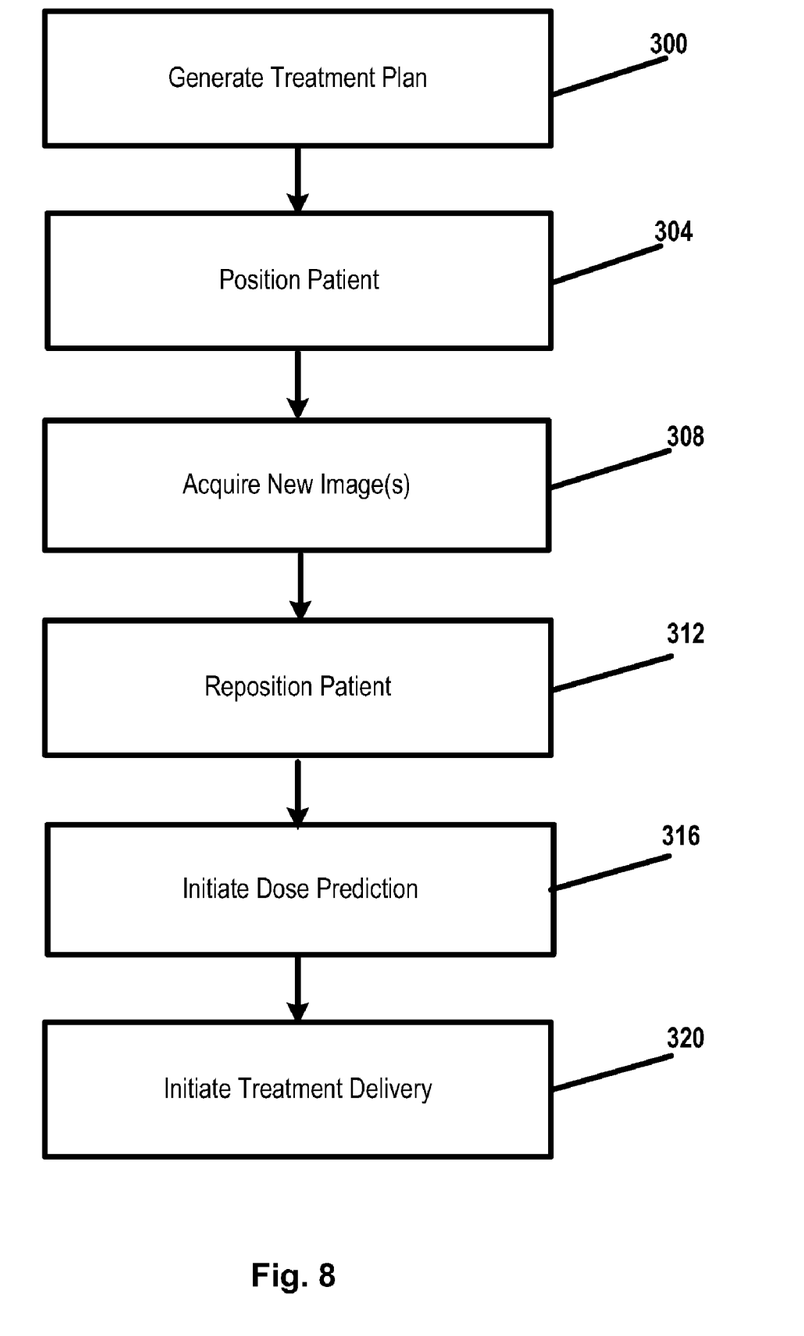
FIG. 8 is a flow chart of a method of predicting a radiation dose to be delivered to a patient according to one embodiment of the present invention.

FIG. 8 illustrates a flow chart of a method of predicting a radiation dose to be delivered to a patient. Medical personnel generate (at 300) a treatment plan for the patient 14 based on patient data, images, or other information. When the patient 14 is ready for a treatment, medical personnel position (at 304) the patient 14 substantially in the treatment position, on the couch 82, with the assistance of the patient positioning module 10 prior to delivery of treatment. While the patient 14 is in the position, the image module 114 acquires (at 308) a new image of the patient 14, which can assist in proper positioning of the patient 14. Additional positioning adjustments can be made as necessary. The medical personnel reposition (at 312) the patient based on the newly-acquired image. The medical personnel initiates (at 316), using the dose prediction module 118, the generation of a predictive radiation dose based on at least one of the images in the treatment plan and the patient's position. Based on the dose prediction, the patient 14 and/or system settings can be adjusted. The medical personnel initiates (at 320) delivery of the treatment with the assistance of the treatment delivery module 122.

Various features and advantages of the invention are set forth in the following claims.

What is claimed is:

1. A method of predicting a radiation dose delivered to a patient in the delivery of a treatment plan to the patient, the patient having a profile, the method comprising:
generating a first image of at least a portion of the patient;
defining a treatment plan for the patient;
generating a second volumetric image of at least a portion of the patient while the patient is substantially in a treatment position;
updating the patient profile with the second image; and
calculating using a computer the radiation dose to be delivered to the patient based upon the patient profile and the treatment plan.

2. A method as set forth in claim 1 wherein the profile is determined at least in part by the actual or intended patient position.

3. A method as set forth in claim 1 wherein the patient profile includes data related to a device that delivers radiation therapy, and wherein the device data is used to predict the radiation dose to be delivered to the patient.

4. A method as set forth in claim 1 wherein the patient profile includes motion data.

5. A method as set forth in claim 1 and further comprising evaluating past data to determine a combination of known dose delivered and predicted dose to be delivered based on the patient profile.

6. A method as set forth in claim 1 and further comprising collecting data during delivery of the treatment plan and comparing the predictive dose to the actual dose delivered to the patient.

7. A method as set forth in claim 1 further comprising changing patient position at least partially in response to the predictive dose.

8. A method as set forth in claim 1 wherein the treatment plan is changed in response to the predictive dose.

9. A method as set forth in claim 7 wherein the patient position is changed during treatment.

10. A method as set forth in claim 7 wherein the patient position is changed after treatment for subsequent treatments.

11. A method as set forth in claim 7 wherein the patient position is changed based on the expected biological effect of the predictive dose delivered.

12. A method as set forth in claim 1 wherein predicting dose to be delivered includes the use of deformable registration.

13. A method as set forth in claim 12 wherein deformable registration is used to identify contours of patient structures.

14. A method as set forth in claim 12 wherein deformable registration is used to determine dose accumulation.

15. A method as set forth in claim 1 further comprising generating a real-time, running predicted dose.

16. A method as set forth in claim 15 and further comprising using feedback to adjust the treatment plan or patient position based on the real-time, running predicted dose.

17. A method as set forth in claim 1 and further comprising acquiring data relating to clinical dose delivered and patient effect, and applying a biological model that relates the predictive dose to the patient effect.

18. A method of determining a radiation dose to be delivered to a patient, the method comprising:
   generating a treatment plan for the patient;
   acquiring a volumetric image of at least a portion of the patient while the patient is substantially in the treatment position;
   calculating using a computer a plurality of doses that would be delivered to the patient for each of a plurality of patient profiles, each patient profile including the acquired image; and
   selecting one of the patient profiles for delivery of the treatment plan.

19. A method as set forth in claim 18 wherein the patient profile includes position data.

20. A method as set forth in claim 18 wherein the patient profile includes motion data.

21. A method as set forth in claim 18 further comprising registering the patient using the acquired image and an image from the treatment plan.

22. A method of determining a radiation dose to be delivered to a patient, the method comprising:
   delivering radiation to a patient according to a predetermined treatment plan;
   acquiring a volumetric image of at least a portion of the patient during delivery of the radiation;
   calculating using a computer a radiation dose while the radiation is being delivered, the radiation dose based on at least in part on the acquired image; and
   determining whether to modify delivery of the radiation while the radiation is being delivered.

23. A method as set forth in claim 22 and further comprising modifying the treatment plan in response to the calculated radiation dose.

24. A method as set forth in claim 22 and further comprising adjusting a position of the patient in response to the calculated radiation dose.

25. A method as set forth in claim 22 and further comprising stopping the delivery of the radiation in response to the calculated radiation dose.

* * * * *